(12) United States Patent
Komplin et al.

(10) Patent No.: US 7,329,785 B2
(45) Date of Patent: Feb. 12, 2008

(54) PROCESS FOR THE PRODUCTION OF 1,3-PROPANEDIOL BY CATALYTIC HYDROGENATION OF 3-HYDROXYPROPANAL IN THE PRESENCE OF A HYDRATION CO-CATALYST

(75) Inventors: Glenn Charles Komplin, Katy, TX (US); Joseph Broun Powell, Houston, TX (US); Paul Richard Weider, Houston, TX (US)

(73) Assignee: Shell Oil Company, Houston, TX (US)

( * ) Notice: Subject to any disclaimer, the term of this patent is extended or adjusted under 35 U.S.C. 154(b) by 179 days.

(21) Appl. No.: 10/958,938

(22) Filed: Oct. 5, 2004

(65) Prior Publication Data

US 2005/0080300 A1    Apr. 14, 2005

Related U.S. Application Data

(60) Provisional application No. 60/509,766, filed on Oct. 7, 2003.

(51) Int. Cl.
*C07C 27/04* (2006.01)
*C07C 29/14* (2006.01)
*C07C 31/18* (2006.01)

(52) U.S. Cl. .................................................... 568/862
(58) Field of Classification Search ................. 568/862
See application file for complete search history.

(56) References Cited

U.S. PATENT DOCUMENTS

| | | | | |
|---|---|---|---|---|
| 4,401,834 | A | 8/1983 | King ............................ | 568/881 |
| 4,876,402 | A | 10/1989 | Logsdon et al. ............. | 568/881 |
| 5,015,789 | A | 5/1991 | Arntz et al. ................. | 568/862 |
| 5,093,537 | A | 3/1992 | Unruh et al. ................ | 568/862 |
| 5,256,827 | A | 10/1993 | Slaugh ........................ | 568/454 |
| 5,276,201 | A * | 1/1994 | Haas et al. .................. | 568/491 |
| 5,304,691 | A | 4/1994 | Arhancet et al. ............ | 568/867 |
| 5,334,778 | A * | 8/1994 | Haas et al. .................. | 568/862 |
| 5,344,993 | A | 9/1994 | Slaugh ........................ | 568/454 |
| 5,364,984 | A | 11/1994 | Arntz et al. ................. | 568/862 |
| 5,364,987 | A * | 11/1994 | Haas et al. .................. | 568/866 |
| 5,585,528 | A | 12/1996 | Powell ........................ | 568/862 |
| 5,786,524 | A | 7/1998 | Powell et al. ............... | 568/862 |
| 5,945,570 | A | 8/1999 | Alhancet ..................... | 568/862 |
| 6,297,408 | B1 | 10/2001 | Haas et al. .................. | 568/862 |
| 2003/0187308 | A1 * | 10/2003 | Haas et al. .................. | 568/862 |
| 2004/0087818 | A1 * | 5/2004 | Brewer et al. .............. | 568/862 |
| 2004/0087819 | A1 * | 5/2004 | Powell et al. ............... | 568/862 |

FOREIGN PATENT DOCUMENTS

| | | |
|---|---|---|
| EP | 572812 | 12/1993 |
| EP | 0 906 258 B1 | 4/1999 |
| WO | 98/57913 | 12/1998 |
| WO | 00/14041 | 3/2000 |
| WO | WO 00/14041 * | 3/2000 |

OTHER PUBLICATIONS

"Atlas of Zeolite Structure Types" (published on behalf of the Structure Commission of the International Zeolite Association), by W.M. Meier, D.H. Olson and Ch. Baerlocher, published by Butterworth-Heinemann, fourth revised edition 1996.
H. P. Boehm, "Chemical Identification of Surface Groups", Institute of Inorganic Chemistry, Univ of Heidelberg, Germany, Advances in Catalysis, vol. 16, p. 179-273, 1968.
T. Okuhara, Chemical Reviews 2002, pp. 3461-3665, "Water-Tolerant Solid Acid Catalysts", 2002.
Written Opinion for PCT/US2004/032754 of Mar. 16, 2005.
Response to First Written Opinion for PCT/US2004/032754 of May 4, 2005.

* cited by examiner

*Primary Examiner*—Yvonne Eyler
*Assistant Examiner*—Kellette Gale
(74) *Attorney, Agent, or Firm*—Richard B. Taylor

(57) ABSTRACT

A process for preparing 1,3-propanediol comprising the steps of: (a) preparing an aqueous mixture of 3-hydroxypropanal, (b) passing said aqueous 3-hydroxypropanal mixture to a hydrogenation zone wherein the hydrogenation zone is comprised of at least two stages wherein the hydrogenation in the first stage is carried out under hydrogenation conditions at a temperature in the range of about 50 to about 130° C. in the presence of a fixed bed or slurry hydrogenation catalyst and wherein an acidic co-catalyst is added or present in at least one of the later stages and the hydrogenation in said later stages is carried out under hydrogenation conditions at a higher temperature than that of the first hydrogenation stage and in the range of about 70 to about 155° C. to form an aqueous solution of 1,3-propanediol; and (c) recovering said 1,3-propanediol.

22 Claims, No Drawings

PROCESS FOR THE PRODUCTION OF 1,3-PROPANEDIOL BY CATALYTIC HYDROGENATION OF 3-HYDROXYPROPANAL IN THE PRESENCE OF A HYDRATION CO-CATALYST

This application claims the benefit of U.S. Provisional Application No. 60/509,766 filed Oct. 7, 2003, the entire disclosure of which is hereby incorporated by reference.

FIELD OF THE INVENTION

The present invention relates to a process for the hydrogenation of 3-hydroxypropanal to 1,3-propanediol. More specifically, the present invention relates to a process incorporating a dual catalyst system which promotes hydration and hydrogenation of by-products to 1,3-propanediol to improve process yields.

BACKGROUND OF THE INVENTION 1,3-propanediol (PDO) can be prepared via hydrogenation of an aqueous solution of 3-hydroxypropanal. The 3-hydroxypropanal (HPA) intermediate solution can be prepared via a process involving the catalyzed hydroformylation (reaction with synthesis gas, $H_2/CO$) of ethylene oxide to form a dilute mixture of HPA in an organic solvent, followed by extraction of the HPA into water to form a more concentrated HPA solution, and subsequent hydrogenation of the HPA to the PDO.

U.S. Pat. No. 5,786,524, which is incorporated herein by reference, describes such a process wherein ethylene oxide and synthesis gas are contacted at 50 to 100° C. and 500 to 5000 psig in the presence of a cobalt or rhodium catalyst and a catalyst promoter to produce an intermediate product mixture comprising HPA. Water is added to the HPA mixture and most of the HPA is extracted into the water to provide an aqueous phase comprising a higher concentration of HPA and an organic phase containing at least a portion of the catalyst. The aqueous phase is separated from the organic phase and then diluted with an aqueous solution of 1,3-propanediol. This aqueous solution is then passed into a hydrogenation zone in contact with a fixed bed hydrogenation catalyst to form an aqueous solution comprising PDO and then the PDO is recovered.

Alternately, hydration of acrolein, as described in U.S. Pat. No. 5,015,789 which is herein incorporated by reference, may be employed to produce the aqueous intermediate stream of 3-hydroxypropanal.

U.S. Pat. No. 5,945,570, which is herein incorporated by reference, describes a novel hydrogenation catalyst for use in the hydrogenation of 3-hydroxypropanal. The catalyst is a promoted nickel catalyst which also comprises molybdenum and a binder material which can be a silicate or an oxide of silicone, zirconium, aluminum, etc. The catalyst system is characterized by a prolonged catalyst life in the hydrogenation reaction environment because of the increased crush strength of the catalyst system with respect to prior catalyst systems such as the supported hydrogenation catalyst system described in U.S. Pat. No. 5,786,524 discussed above.

During the hydrogenation process or in steps preceding the hydrogenation process, significant concentrations of HPA and PDO may coexist. These components may react to form the thermodynamically favored cyclic acetal MW132:

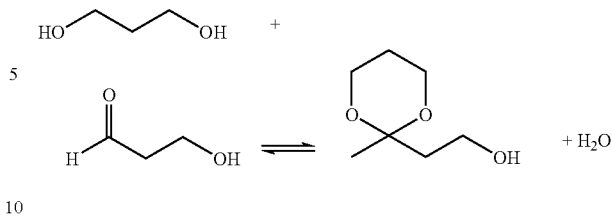

Further reaction of the cyclic acetal may occur, to produce additional byproduct species.

It would be highly advantageous if the reverse reaction, i.e., the reaction of the acetal to PDO could be encouraged during hydrogenation, as this would increase the yield of PDO. However, the extended life catalyst described in U.S. Pat. No. 5,945,570 does not actively promote the reversion of acetal back to PDO and HPA (where the latter would then be hydrogenated to PDO). The current invention allows efficient reversion of acetal byproducts to PDO at improved space-time yields.

SUMMARY OF THE INVENTION

The present invention is a process for preparing 1,3-propanediol comprising the steps of: (a) preparing an aqueous mixture of 3-hydroxypropanal and reaction byproducts, (b) passing the aqueous 3-hydroxypropanal mixture to a hydrogenation zone wherein the hydrogenation zone is comprised of at least two stages wherein the hydrogenation in the first stage is carried out under hydrogenation conditions at a temperature in the range of about 50 to about 130° C. in the presence of a fixed bed or slurry hydrogenation catalyst, and wherein an acidic cocatalyst, which is selected from the group consisting of acidic zeolites, acid form cationic exchange resins, acidic or amphoteric metal oxides, heteropolyacids, and soluble acids is added in or present in at least one of the later stages, and the hydrogenation in said later stages is carried out under hydrogenation conditions at a higher temperature than that of the first hydrogenation stage and in the range of about 70 to about 155° C. to form an aqueous solution of 1,3-propanediol; and (c) recovering said 1,3-propanediol. In a preferred embodiment, the hydrogenation zone is comprised of at least three stages, the hydrogenation in the second stage is carried out at a temperature higher than the temperature of the first stage in the range of about 70 to about 155° C., preferably about 70 to about 140° C., and wherein the acidic cocatalyst is added in or present in the last stage of the hydrogenation zone wherein the hydrogenation in the last stage is carried out under hydrogenation conditions at a temperature higher than the temperature of the second stage and about 120° C. or greater, preferably from about 120° C. to about 155° C. In another preferred embodiment, a slurry hydrogenation catalyst and an acid form cationic exchange resin are used and the temperature in the final hydrogenation stage is from about 100 to about 140° C.

DETAILED DESCRIPTION OF THE INVENTION

A hydroformylation method which can be used to prepare the aqueous mixture of 3-hydroxypropanal from ethylene oxide and synthesis gas, is described in detail in U.S. Pat. No. 5,786,524 which is herein incorporated by reference. U.S. Pat. No. 5,015,789 describes a similar aqueous mixture of 3-hydroxypropanal prepared by hydration of acrolein.

The aqueous stream input to the hydrogenation section is an aqueous solution containing HPA in a concentration within the range of about 3 to about 50 weight percent, preferably about 10 to about 40 weight percent, based on the weight of the aqueous liquid which is usually water. If a fixed-bed catalyst is used for hydrogenation, it is desirable to dilute the concentration of HPA in the feed to the first hydrogenation reactor to a value from about 0.2 to about 15 wt %, and most preferably from about 0.5 to about 8 wt %. Although any aqueous liquid which will not interfere with hydrogenation of HPA, including water, can be used for dilution of the HPA solution to the desired concentration, it is preferred to employ an aqueous PDO-containing solution such as a portion of the product stream from the hydrogenation step. Dilution with such a PDO-containing solution serves to concentrate PDO in the system water, thus avoiding the high cost and recovery of dilute PDO from water which would result from the use of water alone as the diluent. The preferred dilution stream will contain PDO and HPA in an amount within the range of about 20 to about 40 weight percent. The dilution stream will preferably be cooled prior to admixture with the hydroformylation output stream to bring the temperature of the combined stream to that desired for input to the initial stage of fixed-bed hydrogenation.

If a slurry catalyst is used in a backmixed reactor, the extent of reaction of the first stage may be controlled to obtain a similar concentration range of about 0.2 to about 15 wt % HPA, preferably about 0.5 to about 8 wt %, such that predilution of feed is not required.

The hydrogenation process can be carried out in one stage or in two or more sequential temperature stages. In a preferred embodiment, hydrogenation is carried out at a temperature within the range of about 50 to about 130° C., followed by a second stage carried out at a temperature higher than that of the first stage and within the range of about 70 to about 155° C., and then optionally in a third stage at a temperature greater than the temperature of the second stage and with a temperature of about 120° C. or greater, preferably about 120° C. to about 155° C. In this preferred process, the hydrogenation is optionally carried out in two or more separate reaction vessels.

Hydrogenation catalysts useful in converting the aldehyde functional group (as found in HPA), or aldehydes formed via reversion of acetals, to the alcohol functional group (as found in PDO), include Group VIII metals such as nickel, cobalt, iron, palladium, rhodium, ruthenium, and platinum. Copper is also known to be active.

The preferred such hydrogenation catalyst is described in U.S. Pat. No. 5,945,570 which is herein incorporated by reference. The preferred hydrogenation catalyst contains, as the major active component, from about 25 to about 60 wt % nickel (as Ni°), preferably from about 30 to about 45 wt %. The nickel in the active catalyst is predominantly in reduced form. The catalyst contains about 5 to about 20 wt % molybdenum (as Mo°), preferably about 6 to about 16 wt %. The molybdenum is present in the catalyst in both metal and oxide form. The molybdenum has a binding function and is also an activity promoter.

The binder portion of the catalyst acts as a "glue" to hold the separate components together and to provide crush resistance from the pressure drop across the catalyst bed. The binder constitutes about 30 to about 70 wt % of the catalyst and is made up of oxides of silicon, and silicates and oxides of zinc, zirconium, calcium, magnesium and/or aluminum. Typically, the catalyst will contain from about 30 to about 70, preferably about 35 to about 55, wt % silicon; from about 0 to about 2, preferably about 0 to about 1, wt % zinc; and from about 0 to about 2 wt % aluminum. The binder will contain not more than about 2 wt % calcium, and will preferably contain about 0-1 wt % calcium. A preferred embodiment of the catalyst contains essentially no zinc or calcium. The preferred catalyst composition for the first stage of hydrogenation of 3-hydroxypropanal to 1,3-propanediol in aqueous solution contains about 35 wt % nickel and about 8-12 wt % molybdenum, with the balance binder material as described above.

The catalyst can be prepared by any procedure that incorporates the active nickel component, the molybdenum component, and the binder material in a solid bulk form. The preferred catalyst preparation involves mixing nickel oxide, the binder material such as attapulgus clay, and molybdenum trioxide powder into a homogeneous powder. Next, a solution of colloidal silica in sufficient water to form an extrudable mixture is stirred into the solid mixture. The wet mixture is then extruded through a die plate with 0.040-0.070" diameter holes. The extrudates are dried at about 100-125° C. for a time sufficient to reduce the moisture content to less than about 5 wt %. The dried extrudates are then calcined in air at about 450-550° C. for at least about 3 hours until the desired strength is developed. Prior to use, the catalyst is reduced under hydrogen gas at a temperature within the range of about 350 to about 450° C. for a time sufficient for reduction of at least about 60% of the nickel. If the reduced catalyst is not used immediately, it is cooled to ambient and stored under a protective medium such as 1,3-propanediol until used.

In one embodiment of the present invention an acidic cocatalyst is added in a later stage of hydrogenation. The acidic cocatalyst promotes the hydration reaction of the MW132 acetal back to PDO and HPA and thus increases the yield of PDO in the overall hydrogenation process. The acidic cocatalysts useful in the present invention may be selected from acidic zeolites, acid-form cationic exchange resins, heteropolyacids, amphoteric metal oxides exhibiting enhanced acidity relative to the hydrogenation catalyst employed, and soluble acids. They are generally added in an amount from about 1:5 to about 2:1, in ratio with the fixed bed or slurry hydrogenation catalyst. In a highly preferred embodiment, the acidic cocatalyst is added in a third stage of hydrogenation and/or it is used in a post hydrogenation of the aqueous PDO product of the primary hydrogenation.

The acidic cocatalyst may also be included with the fixed bed promoted nickel hydrogenation catalyst in all hydrogenation stages.

Alternately, the acidic cocatalyst may be a soluble acid added or produced as coproduct in the process to obtain a pH from about 2 to about 5.5.

The preferred zeolite catalysts contain one or more modified zeolites preferably in the acidic form. These zeolites should contain pore dimensions large enough to admit the entry of the acyclic or aliphatic compounds. The preferred zeolites include, for example, zeolites of the structural types MFI (e.g., ZSM-5), MEL (e.g., ZSM-11), FER (e.g., ferrierite and ZSM-35), FAU (e.g., zeolite Y), BEA (e.g., beta), MFS (e.g., ZSM-57), NES (e.g. NU-87), MOR (e.g. mordenite), CHA (e.g., chabazite), MTT (e.g., ZSM-23), MWW (e.g., MCM-22 and SSZ-25), EUO (e.g. EU-1, ZSM-50, and TPZ-3), OFF (e.g., offretite), MTW (e.g., ZSM-12) and zeolites ITQ-1, ITQ-2, MCM-56, MCM-49, ZSM-48, SSZ-35, SSZ-39 and zeolites of the mixed crystalline phases such as, for example, zeolite PSH-3. The structural types and references to the synthesis of the various zeolites can be found in the "Atlas of Zeolite Structure Types" (published on behalf of the Structure Commission of the International Zeolite Association), by W. M. Meier, D. H. Olson and Ch. Baerlocher, published by Butterworth-Heinemann, fourth revised edition, 1996. Structural types and references to the zeolites mentioned above are available on the World Wide Web at www.iza-structure.org. Such zeolites are commercially available from Zeolyst International, Inc. and ExxonMobil Corporation. More preferably, the zeolite is a crystalline alumino-silicate that can contain trace amounts of boron from raw materials without on purpose adding boron sources to enrich boron content.

Other suitable catalysts include acid form cation exchange resins. These include the gel type or macroreticular (macroporous) ion exchange resins with sulfonic acid functional groups in acid form, wherein the sulfonic acid function is bonded directly or indirectly to an organic polymer backbone. Examples include: Rohm and Haas AMBERLITE® or AMBERLYST® A200, A252, IR-118, IR120, A15, A35, A36, XN-1010, or uniform particle size A1200 resins; Dow MSC-1 or DOWEX® 50-series resins; SYBRON® C-249, C-267, CFP-110 resins; PUROLITE® C-100 or C-150 resins; RESINTECH® CG8; IWT C-211; SACMP; IWT C-381; and other comparable commercial resins. Another example of these cation exchange resins is NAFION® acidified perfluorinated polymer of sulphonic acid.

Water tolerant solid acid catalysts were recently reviewed by T. Okuhara, in *Chemical Reviews* 2002, pp. 3461-3665, published by The American Chemical Society. Heteropolyacids are formed from two or more different oxyanions and typically include tetrahedrally coordinated silica or phosphorus linked by hexavalent molybdenum, tungsten, uranium, niobium, or tantalum. An acid anion with cesium (Cs2.5) exhibits high activity for acid catalyzed reactions in the presence of water.

Amphoteric or acidic oxides include alumina, silicia, silica alumina, titania, zirconia, and variations thereof included sulfated zirconia, zirconium tungstate, phosphate, molybdate, and niobic acid.

Soluble acid cocatalysts may include mineral acids such as hydrogen chloride, bromide, fluoride, or iodide, as well as nitric acid. Weak acids such as phosphoric, or carboxylic acids such as acetic and proprionic, may be employed.

The metal for the fixed bed hydrogenation catalyst can be a Group VIII metal such as nickel, cobalt, ruthenium, platinum, or palladium, as well as copper, zinc, chromium, and mixtures and alloys of these. The preferred catalysts are particulate nickel-based compositions on water-stable (e.g., ceramic) supports such as the preferred catalyst described in U.S. Pat. No. 5,945,570. The particle size for this catalyst will be that consistent with fixed-bed operation and thus will generally range from about 100 microns to about 3 millimeters, with larger particles giving lower pressure drop at the expense of activity.

EXAMPLE 1

An aqueous PDO solution prepared with ethanol as cosolvent (67 wt %) and containing relatively high amounts (about 5 wt %) of MW132 acetal was hydrogenated in a 500 milliliter batch autoclave reactor to assess the reversion of MW132 acetal and other similar impurities to PDO.

The catalyst, which was the preferred fixed bed promoted nickel hydrogenation catalyst as described in U.S. Pat. No. 5,945,570, showed no reversion of acetal in 5 hours at 150° C. and 1000 psi $H_2$ despite the use of 7.8 wt % catalyst (g-catalyst/g-liquid mixture). The reaction was terminated after a total of 11 hours and 1.5 wt % of acidic USY zeolite was added. 75% of the MW132 acetal was reverted to PDO in the next 2 hours, despite a decrease in temperature of 20° C. to 130° C. A final acetal conversion of 95% was obtained after another 2.5 hours at 150° C. with the acidic zeolite as cocatalyst. The results clearly show the beneficial impact of addition of the zeolite cocatalyst on the rate of reversion of MW132 acetal.

EXAMPLES 2-17

A series of batch hydrogenation experiments were conducted under 1000 psi hydrogen in a 500-ml autoclave using 240 grams of a mixture of 2.7 wt % MW132 acetal in 31 wt % PDO, with water comprising the remaining solvent (Table 1). In all cases, 4 grams of total catalyst were used. For the "Base Case Nickel", 4 grams the preferred catalyst described in U.S. Pat. No. 5,945,570 were employed as the hydrogenation catalyst. Where a cocatalyst was employed, the amount of hydrogenation catalyst was reduced (2 grams) and an equal amount of cocatalyst was employed giving a total of 4 grams of combined catalyst. Samples were withdrawn periodically over a 3-5 hour period for gas chromatographic analysis, to monitor the reaction of M.W. 132 acetal and the formation of n-propanol (NPA), the principal undesired byproduct of acetal reversion to PDO.

A rate constant k was calculated as the slope of the MW132 conversion vs. time, which for a given time "t" can be represented by:

$$k = \frac{-\ln(1-X)}{t \cdot f_{cat}}$$

X is the fractional conversion of MW132 acetal, or $$X = 1 - \frac{[MW132]}{[MW132]_0}$$

where subscript "0" denotes the initial concentration. Parameter $f_{cat}$ represents the weight fraction of catalyst, or the weight of total catalyst (typically 4 grams), divided by the total mass of liquid solution (typically 240 grams).

A selectivity to undesired n-propanol is also defined as the mass of propanol formed relative to the mass of MW132 acetal reverted (principally to PDO and n-propanol).

Given that an optimal high temperature hydrogenation catalyst giving good space time yields will optimize rates and selectivity to desired product (PDO), a Productivity factor "P" was defined as the ratio of MW132 reaction rate divided by propanol selectivity (undesired). Higher values for P thus reflect more economic performance for high temperature reversion of acetals.

Runs 2 and 3 in Table 1 represent base case Ni catalyst replicates with no added cocatalyst. For runs 3-8 (Series "A"), an amphoteric or acid oxide cocatalyst was added, replacing an equivalent amount of base nickel hydrogenation catalyst. Results show that use of cocatalyst enhanced the rate of reversion of MW132 acetal for oxides zirconia, titania, silica, alumina, and silica-alumina. For run #9 (Series "A"), a very acidic $NiO/WO_3$/alumina cocatalyst was added and it also enhanced the rate of acetal reversion relative to the base case with no acid cocatalyst added.

Aqueous acidities of several of the solid oxide cocatalysts were assessed via a backtitration method, entailing contacting overnight at room temperature (with mixing) an aqueous solution of 0.1N potassium hydroxide or carbonate, with solid acid c-ocatalyst, followed by sampling the supertanant for titration with 0.1 N HCl to assess the amount of remaining KOH. The results from this method are shown in Table 2. The oxide co-catalysts tested and the $NiO/WO_3$/alumina catalyst were all substantially more acidic than the nickel base case catalyst, thus explaining their enhanced activity in MW132 reversion. For these experiments, the amount of base (potassium hydroxide or carbonate) was limited to avoid dissolution of the solid oxide. Backtitration of solid oxides for determination of acidity in aqueous media is described by H. P. Boehm, "Chemical Identification of Surface Groups", in *Advances in Catalysis*, Vol. 16, pp. 179-273 (1968).

Increased formation of n-propanol was evident on addition of acidic cocatalyst in Series "A" of Table 1. Series "B" examined a reduction in the temperature of hydrogenation to 130° C. which resulted in a decrease in the amount of undesired n-propanol formed, while still providing an increased rate of reversion of M.W. 132 acetal relative to the base case operated 10° C. hotter at 140° C. The possibility of a temperature reduction is especially attractive because the stability of fixed-bed hydrogenation catalysts in an aqueous environment is known to be adversely impacted by temperature. The current invention allows improved rates to be obtained at a lower temperature than otherwise required for the same space-time conversion, and thereby can extend the life of the high temperature hydrogenation catalyst.

Series C and D (Table 1) examine a soluble organic acid (3-hydroxyproprionic) as the acidic cocatalyst, for a Ru/alumina catalyst and the base case Ni catalyst. For both catalysts, the reversion of M.W. 132 acetal was improved as the reaction mixture was made more acidic via pH adjustment. This result shows that acetal reversion is a function of proton ($H^+$) concentration, as evidenced by pH. A more pH tolerant catalyst in combination with low pH (about 2-5) in the high temperature hydrogenation stage, gives enhanced reversion of acetal heavy ends. The operating pH range for Ni catalysts is about 4-7.5 but it is preferred to keep it above about 5.0, preferably about 5.2 to about 5.5, because otherwise the life of the catalyst is adversely affected. Operation in the range of about 4 to about 5 gives a great increase in the reversion rate.

Series E examines a Raney cobalt slurry catalyst (W. R. Grace #18659-21) operated at a lower temperature of 120° C., amenable to use of sulfonic acid resin (sulfonated polystyrene Amberlyst® 15 from Rohm and Haas) as cocatalyst. No reversion of M.W. 132 acetal could be measured at this temperature in the absence of the strong acid resin cocatalyst. With the resin cocatalyst, the rates were more than twice the nickel base case with only one-half of the amount of undesired n-propanol formation despite operation at 20° C. lower in temperature than for the base case comparison with no acidic cocatalyst. The lower temperature will help to extend the catalyst life while maintaining the ability to revert acetal to PDO.

TABLE 1

Examples 2-17: Acetal Reversion with Acidic Cocatalyst

| Ser | Ex | Hydro cat | Co cat | Hydro cat grams | Acidic co cat grams | Temp ° C. | pH | NPA % selectivity | MW132 rate (1/h) | P = rate/npa 1/h/% |
|---|---|---|---|---|---|---|---|---|---|---|
| A | 2 | Ni-base | None | 4 | 0 | 140 | 5.5 | 11.7 | 12.1 | 1.0 |
| A | 3 | Ni-base | None | 4 | 0 | 140 | 5.5 | 10.8 | 7.3 | 0.7 |
| A | 4 | Ni-base | Zirconia | 2 | 2 | 140 | 5.5 | 14.2 | 24.2 | 1.7 |
| A | 5 | Ni-base | Titania | 2 | 2 | 140 | 5.5 | 16.7 | 44.2 | 2.6 |
| A | 6 | Ni-base | 55/45 silica/alumina | 2 | 2 | 140 | 5.5 | 19.6 | 45.0 | 2.3 |
| A | 7 | Ni-base | Alumina | 2 | 2 | 140 | 5.5 | 22.5 | 34.4 | 1.5 |
| A | 8 | Ni-base | Silica | 2 | 2 | 140 | 5.5 | 24.2 | 40.8 | 1.7 |
| A | 9 | Ni-base | NiO/WO3/alumina | 2 | 2 | 140 | 5.5 | 22.3 | 54.8 | 2.5 |
| B | 2 | Ni-base | None | 4 | 0 | 140 | 5.5 | 11.7 | 12.1 | 1.0 |
| B | 3 | Ni-base | None | 4 | 0 | 140 | 5.5 | 10.8 | 7.3 | 0.7 |
| B | 10 | Ni-base | 55/45 silica/alumina | 2 | 2 | 140 | 5.5 | 19.6 | 45.0 | 2.3 |
| B | 11 | Ni-base | 55/45 silica/alumina | 2 | 2 | 130 | 5.5 | 5.2 | 19.8 | 3.8 |
| C | 12 | Ru/alumina | C3-acid | 4 | n.a. | 140 | 3.9 | 5.6 | 159.7 | 28.7 |
| C | 13 | Ru/alumina | n.a. | 4 | n.a. | 140 | 5.5 | 6.9 | 26.5 | 3.8 |
| D | 14 | Ni-base | C3-acid | 4 | 0 | 140 | 4.4 | 10.7 | 42.3 | 3.9 |
| D | 15 | Ni-base | C3-acid | 4 | 0 | 140 | 5 | 12.7 | 32.7 | 2.6 |
| D | 2 | Ni-base | None | 4 | 0 | 140 | 5.5 | 11.7 | 12.1 | 1.0 |
| D | 3 | Ni-base | None | 4 | 0 | 140 | 5.5 | 10.8 | 7.3 | 0.7 |
| E | 16 | Raney Co | A15 resin | 2 | 2 | 12 | 5.5 | 5.9 | 23.2 | 4.0 |
| E | 17 | Raney Co | None | 2 | 0 | 120 | 5.5 | 0.0 | 0.0 | 0.0 |

Titania Norton #XT25376, ⅟₁₆-inch
Zirconia Engelhard #803A-6-2-31 ⅟₁₆-inch
Alumina AX-200, CRI-Catalysts, ⅟₃₂-inch
Silica Davisil Grade 57, Grace Davison 60/80 mesh
Silica-alumina Ghent 654/CB01-149 CRI-Catalysts, ⅟₁₆-inch
A15 Amberlyst 15 Strong acid resin, Rohm and Haas
1/h = 1/hour - units of space velocity

TABLE 2

Backtitration of Catalyst/
Co-Catalyst Acidity

| Catalyst/Co-cat | Titrant | Catalyst Acidity meq/g |
|---|---|---|
| Ni-base | 0.1N KOH | 0.68 |
| 55/45 silica-alumina | 0.1N KOH | 0.93 |
| Alumina (Ax200) | 0.1N KOH | 0.95 |
| Titania | 0.1N KOH | 0.86 |
| NiO/WO3/alumina | 0.1N KOH | 0.98 |

TABLE 2-continued

Backtitration of Catalyst/
Co-Catalyst Acidity

| Catalyst/Co-cat | Titrant | Catalyst Acidity meq/g |
|---|---|---|
| Ni-base | 0.1K2CO3 | 0.78 |
| None | 0.1K2CO3 | 1.00 |

1.0 meq/g = 100% consumption of base titrant

EXAMPLE 18

Dual continuous-flow reactors were operated with 2.0 grams of a different batch of the catalyst used in the previous examples at 150° C. and 1180 psi (8135 kPa) hydrogen pressure. The liquid flow rates were set to give an average weight hourly space velocity (WHSV) between 0.9 and 1.3, where:

WHSV=grams liquid feed/gram catalyst/hour

Hydrogen was co-fed to the reactor inlet at a flow rate of 8-10 milliliters/minute at standard temperature and pressure, as measured by outlet rotameter, providing operation in the three-phase regime (gas-liquid-solid), as desired for a fixed-bed bubble column reactor. Samples were periodically withdrawn for gas chromatography (GC) analysis of effluent MW132 acetal content. The liquid feed solutions comprised 2.2-2.3 weight percent MW132 acetal in a mixture of 27-31 weight percent PDO in water, adjusted to pH 4.9 via addition of iN KOH for Reactor "A" and to pH 5.5 for Reactor "B". This example simulates the feed to a final high temperature hydrogenation stage. A rate constant for acetal reversion was computed as described above. For a fixed bed catalyst such as used in this example, $f_{cat}=1$.

The results for a one-month run are shown in Table 3. Reactor A with feed having a pH of 4.9 showed less MW132 in the effluent than Reactor B which was operated with a feed having a pH of 5.5. The rate constant (calculated as described above) indicated a catalytic activity approximately two times greater at pH 4.9 vs. that observed with pH 5.5 feed. This experiment establishes that the advantage of operation at a lower pH to enhance the rate of reversion of cyclic acetals is indeed sustained during continuous operation for a commercially significant period of time.

TABLE 3

Continuous-Flow Micro-Reactor Test of pH Impact on Acetal Reversion

| | Reactor A: pH 4.9 feed 2.22 wt % MW132 | | | | Reactor B: pH 5.5 feed 2.29 wt % MW132 | | | |
|---|---|---|---|---|---|---|---|---|
| Day | Total g-feed/ g-catalyst | WHSV | Outlet MW132 wt % | rate const. 1/h | Total g-feed/ g-catalyst | WHSV | Outlet MW132 wt % | rate const. 1/h |
| 0.00 | 0.0 | n.a | n.a | n.a | 0.0 | n.a | n.a | n.a |
| 6.00 | 137.1 | 0.95 | 0.295 | 1.92 | 157.6 | 1.09 | 0.438 | 1.78 |
| 7.00 | 159.4 | 0.93 | 0.166 | 2.41 | 177.4 | 0.83 | 0.265 | 1.75 |
| 8.00 | 182.6 | 0.97 | 0.112 | 2.89 | 192.1 | 0.61 | 0.124 | 1.77 |
| 9.00 | 206.2 | 0.98 | 0.055 | 3.64 | 219.2 | 1.13 | 0.251 | 2.46 |
| 12.00 | 267.4 | 0.85 | 0.046 | 3.29 | 270.5 | 0.71 | 0.105 | 2.17 |
| 26.00 | 649.0 | 1.14 | 0.001 | 8.75 | 795.2 | 1.56 | 0.248 | 3.42 |
| 27.00 | 676.2 | 1.13 | 0.001 | 8.73 | 818.9 | 0.99 | 0.125 | 2.84 |
| 28.00 | 703.5 | 1.14 | 0.001 | 8.78 | 841.4 | 0.94 | 0.131 | 2.65 |
| 29.00 | 731.1 | 1.15 | 0.001 | 8.85 | 871.6 | 1.26 | 0.154 | 3.36 |

We claim:

1. A process for preparing 1,3-propanediol via hydrogenation of 3-hydroxypropanal comprising the steps of:
   (a) preparing an aqueous mixture of 3-hydroxypropanal,
   (b) passing the aqueous 3-hydroxypropanal mixture to a hydrogenation zone wherein the hydrogenation zone is comprised of at least two stages wherein the hydrogenation in the first stage is carried out under hydrogenation conditions at a temperature in the range of about 50 to about 130° C. in the presence of a fixed bed or slurry hydrogenation catalyst and wherein an acidic cocatalyst, which is selected from the group consisting of acidic zeolites, acid form cationic exchange resins, heteropolyacids, and soluble acids, is added in or present in at least one of the later stages, and the hydrogenation in said later stages is carried out under hydrogenation conditions at a higher temperature than that of the first hydrogenation stage and in the range of about 70 to about 155° C. in the presence of a fixed bed or slurry hydrogenation catalyst to form an aqueous solution of 1,3-propanediol, wherein when the acidic cocatalyst is a soluble acid the soluble acid provides a pH from about 2 to about 5.5; and
   (c) recovering said 1,3-propanediol.

2. The process of claim 1 wherein the hydrogenation zone is comprised of at least three stages wherein the hydrogenation in the second stage is carried out under hydrogenation conditions at a temperature higher than the temperature of the first stage in the range of about 70 to about 155° C. and the acidic cocatalyst is added in or present in the last stage of the hydrogenation zone wherein the hydrogenation in the last stage is carried out under hydrogenation conditions at a temperature higher than the temperature of the second stage and about 120° C. or greater.

3. The process of claim 2 wherein the temperature in the second stage is from about 70 to about 140° C. and the temperature in the last stage is from about 120 to about 155° C.

4. The process of claim 1 wherein the pH in step (b) is above about 5.

5. The process of claim 4 wherein the pH in step (b) is from about 5.2 to about 5.5.

6. The process of claim 5 wherein the acid cocatalyst is a soluble acid which is added to the process or produced as a coproduct.

7. The process of claim 1 wherein a slurry hydrogenation catalyst and an acid cationic exchange resin are used and the temperature in the final hydrogenation stage is from about 100 to about 140° C.

8. The process of claim 1 wherein the aqueous 3-hydroxypropanal mixture passed to the hydrogenation zone is an aqueous solution containing 3-hydroxypropanal at a concentration of from about 3 to about 50 wt % based on the weight of the aqueous solvent.

9. The process of claim 8 wherein the aqueous 3-hydroxypropanal mixture passed to the hydrogenation zone is an aqueous solution containing 3-hydroxypropanal at a concentration of from about 10 to about 40 wt % based on the weight of the aqueous solvent.

10. The process of claim 8 wherein a fixed bed catalyst is used for hydrogenation and the concentration of 3-hydroxypropanal in the aqueous 3-hydroxypropanal mixture passed to the hydrogenation zone is from about 0.2 to about 15 wt % based on the weight of the aqueous solvent.

11. The process of claim 10 wherein the aqueous 3-hydroxypropanal mixture of step a) is diluted to from about 0.2 to about 15 wt % based on the weight of the aqueous solvent by the addition of an aqueous solution of 1,3-propanediol.

12. The process of claim 11 wherein the total amount of 3-hydroxypropanal and 1,3-propanediol in the diluted mixture is from about 20 to about 40 wt % based on the weight of the aqueous solvent.

13. The process of claim 12 wherein the aqueous solution of 1,3-propanediol is cooled prior to its addition to the aqueous 3-hydroxypropanal mixture of step a).

14. The process of claim 10 wherein a fixed bed catalyst is used for hydrogenation and the concentration of 3-hydroxypropanal in the aqueous 3-hydroxypropanal mixture passed to the hydrogenation zone is from about 0.5 to about 8 wt % based on the weight of the aqueous solvent.

15. The process of claim 14 wherein the aqueous 3-hydroxypropanal mixture of step a) is diluted to from about 0.5 to about 8 wt % based on the weight of the aqueous solvent by the addition of an aqueous solution of 1,3-propanediol.

16. The process of claim 15 wherein the total amount of 3-hydroxypropanal and 1,3-propanediol in the diluted mixture is from about 20 to about 40 wt % based on the weight of the aqueous solvent.

17. The process of claim 16 wherein the aqueous solution of 1,3-propanediol is cooled prior to its addition to the aqueous 3-hydroxypropanal mixture of step a).

18. The process of claim 1 wherein a fixed bed hydrogenation catalyst is used and the acidic cocatalyst is added with the hydrogenation catalyst in all hydrogenation stages.

19. The process of claim 1 wherein the acidic cocatalyst is added in at least one of the later hydrogenation stages.

20. The process of claim 1 wherein the soluble acid is selected from the group consisting of mineral acids, phosphoric acid, acetic acid, propionic acid, and 3-hydroxypropionic acid.

21. A process for preparing 1,3-propanediol via hydrogenation of 3-hydroxypropanal comprising the steps of:

(a) preparing an aqueous mixture of 3-hydroxypropanal, (b) passing the aqueous 3-hydroxypropanal mixture to a hydrogenation zone wherein the hydrogenation zone is comprised of at least two stages wherein the hydrogenation in the first stage is carried out under hydrogenation conditions at a temperature in the range of about 50 to about 130° C. in the presence of a fixed bed or slurry hydrogenation catalyst and wherein an acidic cocatalyst, which is selected from the group consisting of acidic or amphoteric metal oxides, is added in or present in at least one of the later stages in a ratio of 1:5 to 2:1 with the fixed bed or slurry hydrogenation catalyst, and the hydrogenation in said later stages is carried out under hydrogenation conditions at a higher temperature than that of the first hydrogenation stage and in the range of about 70 to about 155° C. in the presence of a fixed bed or slurry hydrogenation catalyst to form an aqueous solution of 1,3-propanediol; and (c) recovering said 1,3-propanediol.

22. A process for preparing 1,3-propanediol via hydrogenation of 3-hydroxypropanal comprising the steps of:

(a) preparing an aqueous mixture of 3-hydroxypropanal and 1,3-propanediol, (b) passing the aqueous 3-hydroxypropanal, 1,3-propanediol mixture to a hydrogenation zone wherein the hydrogenation zone is comprised of at least two stages wherein the hydrogenation in the first stage is carried out under hydrogenation conditions at a temperature in the range of about 50 to about 130° C. in the presence of a fixed bed or slurry hydrogenation catalyst and wherein an acidic cocatalyst, which is selected from the group consisting of acidic or amphoteric metal oxides, is added in or present in at least one of the later stages, and the hydrogenation in said later stages is carried out under hydrogenation conditions at a higher temperature than that of the first hydrogenation stage and in the range of about 70 to about 155° C. in the presence of a fixed bed or slurry hydrogenation catalyst to form an aqueous solution of 1,3-propanediol; and (c) recovering said 1,3-propanediol.

* * * * *